US011612380B2

(12) United States Patent
Imahashi

(10) Patent No.: US 11,612,380 B2
(45) Date of Patent: Mar. 28, 2023

(54) ULTRASOUND ENDOSCOPE

(71) Applicant: OLYMPUS CORPORATION, Tokyo (JP)

(72) Inventor: Takuya Imahashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 73 days.

(21) Appl. No.: 16/785,900

(22) Filed: Feb. 10, 2020

(65) Prior Publication Data
US 2020/0170621 A1 Jun. 4, 2020

Related U.S. Application Data

(63) Continuation of application No. PCT/JP2018/030446, filed on Aug. 16, 2018.

(30) Foreign Application Priority Data

Aug. 22, 2017 (JP) .............................. JP2017-159440

(51) Int. Cl.
*A61B 8/00* (2006.01)
*A61B 8/12* (2006.01)
(Continued)

(52) U.S. Cl.
CPC .......... *A61B 8/4494* (2013.01); *A61B 8/0841* (2013.01); *A61B 8/12* (2013.01); *A61B 8/4411* (2013.01); *A61B 1/018* (2013.01)

(58) Field of Classification Search
CPC ....... A61B 8/4494; A61B 8/0841; A61B 8/12; A61B 8/4411; A61B 1/018
See application file for complete search history.

(56) References Cited

U.S. PATENT DOCUMENTS

| 6,319,197 | B1 * | 11/2001 | Tsuji | ...................... | H04N 7/183 |
| | | | | | 348/E7.087 |
| 7,355,625 | B1 * | 4/2008 | Mochida | ................ | H04N 7/183 |
| | | | | | 348/65 |
| 8,517,949 | B2 | 8/2013 | Hiraoka | | |
| 10,234,431 | B2 | 3/2019 | Kandori | | |

(Continued)

FOREIGN PATENT DOCUMENTS

| CN | 103108594 A | 5/2013 |
| CN | 203935186 U | 11/2014 |

(Continued)

OTHER PUBLICATIONS

Machine-generated English translation of Saiga et al. (JP 2001-104311) (Year: 2022).*

(Continued)

*Primary Examiner* — Pascal M Bui Pho
*Assistant Examiner* — Taylor Deutsch
(74) *Attorney, Agent, or Firm* — Scully, Scott, Murphy & Presser, P.C.

(57) ABSTRACT

An ultrasound endoscope includes: an insertion portion to be inserted into a subject; an ultrasound transducer that is provided at a distal end of the insertion portion and includes plural piezoelectric element groups configured to transmit and receive ultrasound; a connector portion that is provided on a proximal end side of the insertion portion and includes plural connectors to which an external device is connected; and a cable portion including plural first coaxial lines connected to the piezoelectric element groups configured to transmit the ultrasound to a first area, and plural second coaxial lines connected to the piezoelectric element groups configured to transmit the ultrasound to a second area, the first coaxial lines being shorter in length than the second coaxial lines, the first area and the second area being where the ultrasound is transmitted.

13 Claims, 5 Drawing Sheets

(51) Int. Cl.
*A61B 8/08* (2006.01)
*A61B 1/018* (2006.01)

(56) References Cited

U.S. PATENT DOCUMENTS

| | | | |
|---|---|---|---|
| 2005/0143658 A1 | 6/2005 | Saiga | |
| 2008/0200814 A1* | 8/2008 | Imahashi | A61B 8/445 600/463 |
| 2009/0256934 A1* | 10/2009 | Usami | A61B 1/00059 348/241 |
| 2011/0160588 A1* | 6/2011 | Ichikawa | A61B 8/465 600/443 |
| 2012/0274752 A1* | 11/2012 | Hashimoto | A61B 1/00009 348/65 |
| 2012/0310045 A1* | 12/2012 | Hu | A61B 1/0051 600/110 |
| 2013/0072801 A1* | 3/2013 | Hiraoka | A61B 1/00 600/463 |
| 2014/0046190 A1* | 2/2014 | Ogawa | A61B 8/4444 600/462 |
| 2019/0020507 A1* | 1/2019 | Hornbach | A61B 1/00009 |

FOREIGN PATENT DOCUMENTS

| | | | |
|---|---|---|---|
| CN | 106501373 A | | 3/2017 |
| JP | H069613 Y2 | * | 3/1994 |
| JP | 2000-139927 A | | 5/2000 |
| JP | 2000-166928 A | | 6/2000 |
| JP | 2001-104311 A | | 4/2001 |
| JP | 2005-192640 A | | 7/2005 |
| JP | 2017-074231 A | | 4/2017 |

OTHER PUBLICATIONS

Machine-generated English translation of JP-H069613-Y2, with publication date Mar. 16, 1994 (Year: 2022).*
International Search Report dated Nov. 6, 2018 issued in PCT/JP2018/030446.
Chinese Office Action dated December Dec. 31, 2021 received with 201880053392.4.
Chinese Office Action dated Sep. 5, 2022 received in 201880053392.4.

* cited by examiner

PROXIMAL END SIDE ←——→ DISTAL END SIDE
INSERTION DIRECTION

PROXIMAL END SIDE ←——→ DISTAL END SIDE
INSERTION DIRECTION

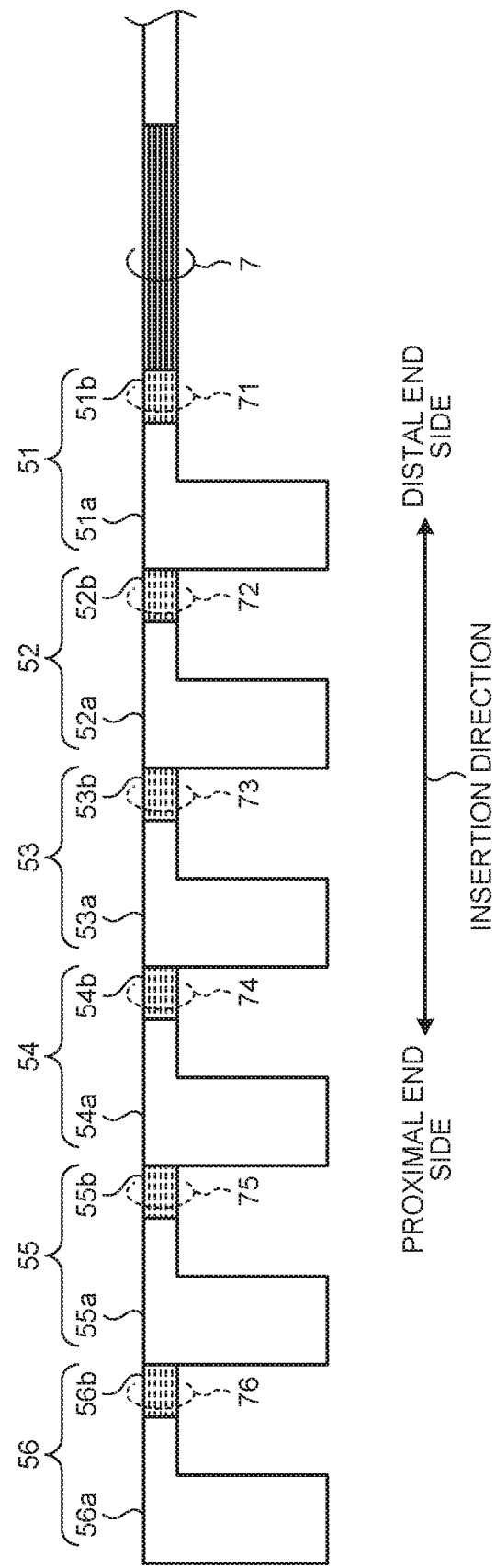

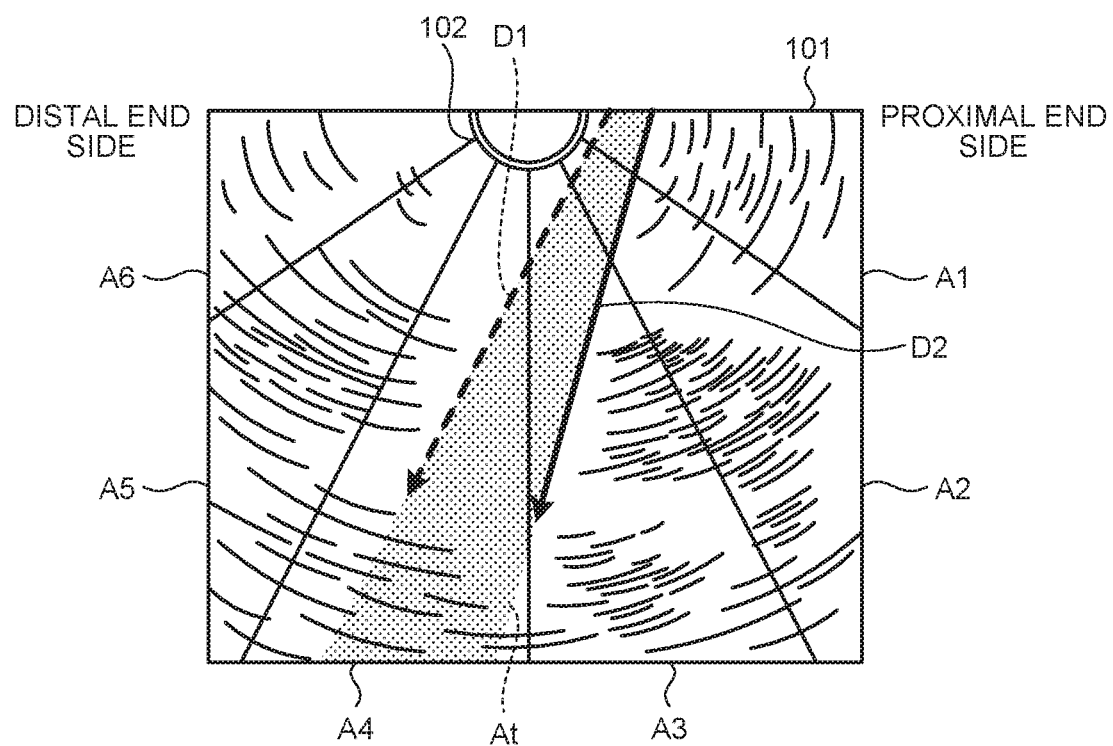

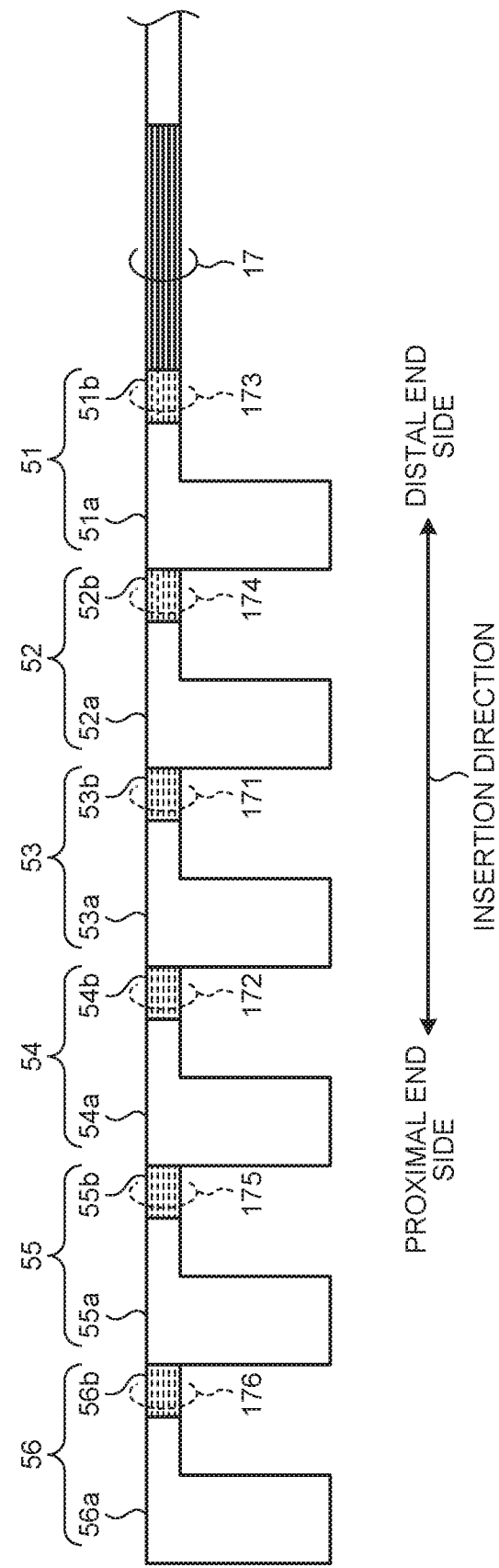

ULTRASOUND ENDOSCOPE

CROSS-REFERENCE TO RELATED APPLICATION

This application is a continuation of PCT International Application No. PCT/JP2018/030446 filed on Aug. 16, 2018, which designates the United States, incorporated herein by reference, and which claims the benefit of priority from Japanese Patent Application No. 2017-159440, filed on Aug. 22, 2017, incorporated herein by reference.

BACKGROUND

1. Technical Field

The present disclosure relates to an ultrasound endoscope.

2. Related Art

Known as a technique for observation of characteristics inside a subject is an ultrasound endoscope that transmits and receives ultrasound by means of a group of ultrasound transducers provided at a distal end of an insertion portion inserted into the subject (as seen in, for example, Japanese Patent Application Laid-open No. 2001-104311). The ultrasound endoscope transmits ultrasound from the ultrasound transducers, and receives, by means of the ultrasound transducers, ultrasound echoes reflected inside the subject, and an ultrasound observation device enables observation of an observation target by generating, based on signals received, an ultrasound image. The ultrasound endoscope is connected to the ultrasound observation device via a connector. Upon this connection, treatment may be performed by insertion of a treatment tool into an instrument channel. Furthermore, one coaxial line is connected to each ultrasound transducer in the group of ultrasound transducers, and the total number of coaxial lines is generally 50 or more.

SUMMARY

In some embodiments, An ultrasound endoscope includes: an insertion portion to be inserted into a subject; an ultrasound transducer that is provided at a distal end of the insertion portion and includes plural piezoelectric element groups configured to transmit and receive ultrasound; a connector portion that is provided on a proximal end side of the insertion portion and includes plural connectors to which an external device is connected; and a cable portion including plural first coaxial lines connected to the piezoelectric element groups configured to transmit the ultrasound to a first area, and plural second coaxial lines connected to the piezoelectric element groups configured to transmit the ultrasound to a second area, the first coaxial lines being shorter in length than the second coaxial lines, the first area and the second area being where the ultrasound is transmitted.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a schematic diagram illustrating an internal configuration of a connector portion illustrated in FIG. 1;

FIG. 5 is a diagram illustrating an example of an ultrasound image captured by the ultrasound endoscope illustrated in FIG. 1; and FIG. 6 is a schematic diagram illustrating an internal configuration of a connector portion according to a modified example of the embodiment.

DETAILED DESCRIPTION

Described hereinafter by reference to the drawings are embodiments of an ultrasound endoscope according to the disclosure. The disclosure is not limited by these embodiments. The disclosure is generally applicable to ultrasound endoscopes where treatment tools are used.

Furthermore, any elements that are the same or corresponding to each other are assigned with the same reference sign throughout the drawings, as appropriate. Moreover, it needs to be noted that the drawings are schematic and relations among dimensions of each element therein and proportions among the elements therein may be different from the actual ones. The drawings may also include a portion that differs in relations among its dimensions or portions that differ in their proportions among the drawings.

Embodiments

Figure 1:
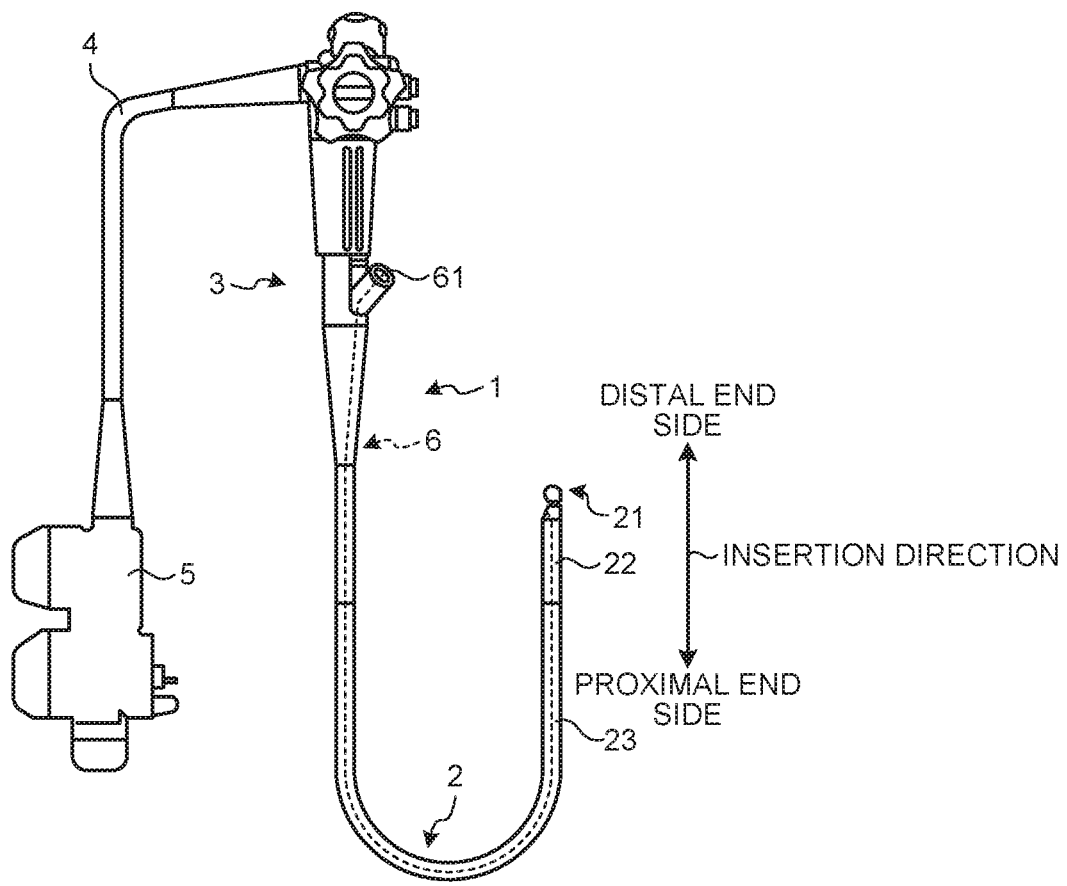
FIG. 1 is a schematic diagram illustrating a configuration of an ultrasound endoscope according to an embodiment of the disclosure.

FIG. 1 is a schematic diagram illustrating a configuration of an ultrasound endoscope according to an embodiment of the disclosure. An ultrasound endoscope 1 includes: an insertion portion 2 that has an imaging unit provided at a distal end of the insertion portion 2 and is inserted into a subject; an operating unit 3 that is provided consecutively to the insertion portion 2 on a proximal end side of the insertion portion 2; a universal cord 4 extending from a side portion of the operating unit 3; a connector portion 5 that is provided consecutively to the universal cord 4 and is connected to an observation device that controls the ultrasound endoscope 1 and to a light source device for supply of illumination light to the ultrasound endoscope 1; an instrument channel 6 that allows a treatment tool as a therapeutic accessory to be protruded from the distal end of the insertion portion 2, the treatment tool having been inserted from a proximal end portion of the insertion portion 2; and a cable portion described later. In this specification, as illustrated in FIG. 1, a direction along which the insertion portion 2 is inserted will be referred to as the "insertion direction", and the direction in which the insertion portion 2 is located relative to the operating unit 3 (the upward direction in FIG. 1) will be referred to as the "distal end side", and the direction in which the connector portion 5 is located relative to the operating unit (the downward direction in FIG. 1) will be referred to as the "proximal end side".

The insertion portion 2 has: an ultrasound transducer 21 provided at the distal end of the insertion portion 2; a bending portion 22 that is provided on a proximal end side of the ultrasound transducer 21 and is bendable; and a flexible tube portion 23 that is provided on a proximal end side of the bending portion 22 and has flexibility. A proximal end of the flexible tube portion 23 is provided consecutively to the operating unit 3 on a distal end side of the operating unit 3.

Figure 2:
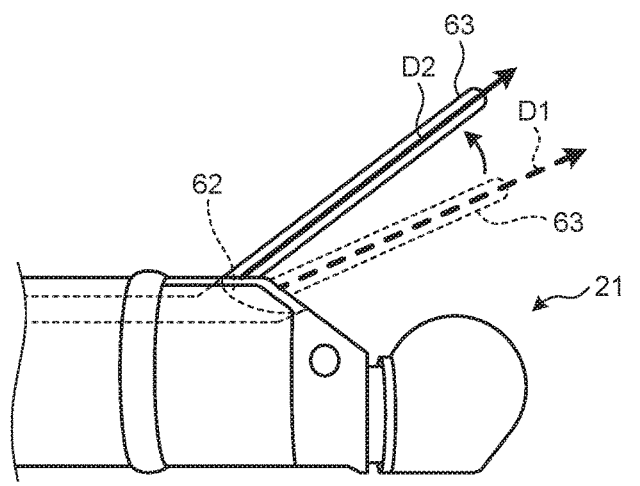
FIG. 2 is a partial enlarged view of an ultrasound transducer in the ultrasound endoscope illustrated in FIG. 1.
Figure 3:
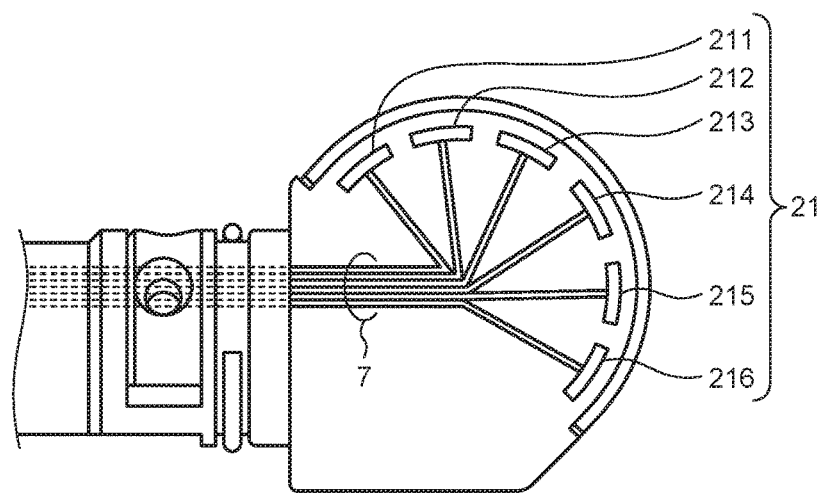
FIG. 3 is a schematic diagram illustrating an internal configuration of the ultrasound transducer in FIG. 2.

FIG. 2 is a partial enlarged view of an ultrasound transducer in the ultrasound endoscope illustrated in FIG. 1. FIG. 3 is a schematic diagram illustrating an internal configuration of the ultrasound transducer in FIG. 2. The ultrasound transducer 21 includes multiple piezoelectric elements that transmit and receive ultrasound, and in FIG. 3, these multiple piezoelectric elements are grouped into six groups, which are illustrated as piezoelectric element groups 211 to 216. The ultrasound transducer 21 may be a convex transducer or a linear transducer. According to this embodiment, the ultrasound transducer 21 is a convex ultrasound transducer that includes the piezoelectric element groups 211 to 216 arranged in an arc shape and that performs electronic scanning by electronic switch-over among the piezoelectric elements in the piezoelectric element groups 211 to 216 related to the transmission and reception.

FIG. 4 is a schematic diagram illustrating an internal configuration of a connector portion illustrated in FIG. 1. As illustrated in FIG. 4, the connector portion 5 includes connectors 51 to 56. The connectors 51 to 56 are each formed of a flexible printed circuit (FPC) or a small-size connector and include: substrates 51a to 56a each connected to a connecting terminal connected to an external device; and connecting portions 51b to 56b that connect the substrates 51a to 56a and coaxial line groups 71 to 76 to each other. The external device is, for example, an ultrasound observation device. The connector 51 is located at the most distal end side of the connector portion 5 and the connector 56 is located at the most proximal end side of the connector portion 5. In other words, the connector 51 is closest to the ultrasound transducer 21 and the connector 56 is farthest from the ultrasound transducer 21.

As illustrated in FIG. 1, the instrument channel 6 includes an instrument channel port 61 provided on a proximal end side of the insertion portion 2. Furthermore, as illustrated in FIG. 2, on a distal end side of the insertion portion 2, the instrument channel 6 includes an instrument channel outlet 62 provided on a proximal end side of the ultrasound transducer 21. Specifically, a distal end of the bending portion 22 has a distal end rigid portion fixed thereto, the distal end rigid portion being where the ultrasound transducer 21 is installed, and the distal end rigid portion includes the instrument channel outlet 62 formed therein, the instrument channel outlet 62 being an outlet of the instrument channel 6. The instrument channel 6 allows a treatment tool 63 to be protruded from the instrument channel outlet 62, the treatment tool 63 being, for example, a puncture needle, which has been inserted from the instrument channel port 61. A direction D1 indicated by a broken-lined arrow in FIG. 2 represents a state before the treatment tool 63 is raised. In contrast, a direction D2 indicated by a solid-lined arrow in FIG. 2 represents a state where the treatment tool 63 has been raised by a treatment tool raising base not illustrated in the drawings. Therefore, a region between the direction D1 and the direction D2 is a region where the treatment tool 63 is likely to pass. In other words, the treatment tool 63 is able to be protruded in the region between the direction D1 and the direction D2. The treatment tool raising base is able to be raised by a predetermined operation being performed on the operating unit 3.

As illustrated in FIG. 4, a cable portion 7 includes the plural coaxial line groups 71 to 76. The coaxial line 71 to 76 respectively connect the piezoelectric element groups 211 to 216 and the connectors 51 to 56 to each other electrically in this order.

FIG. 5 is a diagram illustrating an example of an ultrasound image captured by the ultrasound endoscope illustrated in FIG. 1. As illustrated in FIG. 5, an ultrasound image 101 includes a transducer area 102 corresponding to the ultrasound transducer 21. The ultrasound image 101 is an image, in which an area of 180 degrees about the transducer area 102 has been captured, and a direction D1 and a direction D2 illustrated in FIG. 5 respectively correspond to the direction D1 and the direction D2 illustrated in FIG. 2. Therefore, an area At between the direction D1 and the direction D2 in the ultrasound image 101 is an area where the treatment tool 63 is likely to pass. Furthermore, areas A1 to A6 in FIG. 5 are areas over which the piezoelectric element groups 211 to 216 respectively transmit ultrasound. The areas over which the piezoelectric element groups 211 to 216 transmit ultrasound overlap each other because ultrasound is propagated while spreading radially, but for simplified explanation, in this specification, description is made by association between the piezoelectric element groups 211 to 216 and the areas A1 to A6.

Distal end portions of the coaxial line groups 71 to 76 of the cable portion 7 connected to the piezoelectric element groups 211 to 216 illustrated in FIG. 3 have the same lengths. On the contrary, the coaxial line groups 71 to 76 illustrated in FIG. 4 extend respectively to the connecting portions 51b to 56b and increase in length in order from the coaxial line group 71 to the coaxial line group 76. That is, in the cable portion 7, the coaxial line groups 71 to 74 connected to the piezoelectric element groups 211 to 214 that transmit ultrasound to the area At where the treatment tool 63 protruded from the instrument channel outlet 62 is likely to pass are shorter in length than the coaxial line groups 75 and 76 connected to the piezoelectric element groups 215 and 216 that transmit ultrasound to the areas A5 and A6 where the treatment tool 63 protruded from the instrument channel outlet 62 does not pass. Furthermore, in the cable portion 7, the shorter the shortest distance from a piezoelectric element group to the area At where the treatment tool 63 protruded from the instrument channel outlet 62 is likely to pass is (that is, the closer the piezoelectric element group is to the piezoelectric element group 211), the shorter in length the coaxial line group connected to that piezoelectric element group is (that is, the coaxial line group 71 that is connected to the piezoelectric element group 211 is shorter in length than another piezoelectric element group that is connected to another piezoelectric element group).

The shorter the length of a coaxial line is, the more reduced attenuation of a received signal received by a piezoelectric element corresponding thereto is able to be. Therefore, since the coaxial line groups 76 to 71 decrease in length in this order in the cable portion 7, an ultrasound image is able to be depicted with clearer image quality toward the area A1. For example, if the coaxial line groups 71 to 76 differ from each other in length by 20 mm each, the coaxial line group 71 and the coaxial line group 76 may differ from each other by about 1 dB.

As described above, according to the embodiment, because the coaxial line groups 71 to 74 are shorter in length than the coaxial line groups 75 and 76, the area At in the ultrasound image 101 is able to be depicted with clearer image quality, the area At being where the treatment tool 63 protruded from the instrument channel outlet 62 is likely to pass, the coaxial line groups 71 to 74 being connected to the piezoelectric element groups 211 to 214 that transmit ultrasound to the area At, the coaxial line groups 75 and 76 being connected to the piezoelectric element groups 215 and 216 that transmit ultrasound to the areas A5 and A6 where the treatment tool 63 protruded from the instrument channel outlet 62 does not pass.

Furthermore, according to the embodiment, the coaxial line groups 76 to 71 decrease in length in order from the coaxial line group 76 connected to the piezoelectric element group 216 to the coaxial line group 71 connected to the piezoelectric element group 211, and when treatment by use of the treatment tool 63, which is, for example, a puncture needle, is performed, an image at a position where the puncture needle starts to puncture a living body is able to be observed with clearer image quality, the image being particularly important in the treatment.

Furthermore, according to the embodiment, the image quality is able to be made clear without increase in the thickness of each coaxial line. As a result, the image quality is able to be made clear, while increase in the burden on the patient due to increase in the thickness of the insertion portion 2 is able to be avoided. Moreover, according to the embodiment, because image quality is able to be made clear by use of a configuration that has been used in the related art, the cost is inexpensive.

Modified Example

FIG. 6 is a schematic diagram illustrating an internal configuration of a connector portion according to a modified example of the embodiment. As illustrated in FIG. 6, in a cable portion 17 of an ultrasound endoscope according to the modified example of the embodiment, a coaxial line group 171 is connected to a connecting portion 53b, a coaxial line group 172 is connected to a connecting portion 54b, a coaxial line group 173 is connected to a connecting portion 51b, a coaxial line group 174 is connected to a connecting portion 52b, a coaxial line group 175 is connected to a connecting portion 55b, and a coaxial line group 176 is connected to a connecting portion 56b. That is, in the cable portion 17, among piezoelectric element groups 211 to 214 that transmit ultrasound to an area At where a treatment tool 63 protruded from an instrument channel outlet 62 is likely to pass, coaxial line groups (the coaxial line groups 173 and 174) connected to piezoelectric element groups (the piezoelectric element groups 213 and 214) arranged at positions closer to the center of the piezoelectric element groups 211 to 216 that have been arranged (between the piezoelectric element group 213 and the piezoelectric element group 214) are shorter in length. As a result, according to the modified example, the center (areas A3 and A4) of an ultrasound image 101 is able to be depicted with clearer image quality. When treatment is performed by use of the treatment tool 63, the treatment is performed by placement of a lesion, which is captured in the ultrasound image 101, at the center of the ultrasound image 101. Therefore, according to the modified example, the treatment is able to be performed while observation around the lesion is performed with clear image quality.

The ways in which the coaxial line groups and the connecting portions are connected to each other are not limited to those according to the embodiment and modified example described above. At least one of coaxial line groups connected to the piezoelectric element groups 211 to 214 that transmit ultrasound to the area At where the treatment tool 63 protruded from the instrument channel outlet 62 is likely to pass is preferably shorter than coaxial line groups connected to the piezoelectric element groups 215 and 216 that transmit ultrasound to areas (the areas A5 and A6) where the treatment tool 63 protruded from the instrument channel outlet 62 does not pass, and the image in the area/areas mainly depicted by the piezoelectric element group/groups connected to the shorter coaxial line group/groups is thereby able to be made clear. In other words, by connection of the longest coaxial line groups 75 and 76 of the coaxial line groups 71 to 76 to the piezoelectric element groups 215 and 216 that transmit ultrasound to areas (the areas A5 and A6) where the treatment tool 63 protruded from the instrument channel outlet 62 does not pass, the areas, in which the image is most unclear, are able to be placed outside an area where treatment is performed.

Furthermore, an ultrasound endoscope in which the treatment tool raising base raises the treatment tool 63 has been described above with respect to the embodiment, but the embodiment is not limited to this ultrasound endoscope. For example, in an ultrasound endoscope not having a treatment tool raising base, such as an ultrasound endoscope for bronchi or a direct viewing type ultrasound endoscope, a coaxial line connected to a piezoelectric element group that transmits ultrasound to an area At may be made shorter, the area At being an area including the direction in which a treatment tool 63 is protruded, the direction being determined by the shape of an instrument channel outlet 62.

Realized according to the disclosure is an ultrasound endoscope that enables depiction of an area with clearer image quality, the area being in an ultrasound image and being where a treatment tool is likely to pass.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope, comprising:
an insertion portion configured to be inserted into a subject;
an ultrasound transducer provided at a distal end of the insertion portion, the ultrasound transducer comprising plural piezoelectric element groups configured to transmit ultrasound to a first area and to a second area and to receive the ultrasound from the first area and from the second area;
an instrument channel configured to accommodate an instrument therein, the instrument channel having an instrument channel outlet from which the instrument protrudes, the instrument channel outlet being disposed proximally relative to the ultrasound transducer;
a connector portion provided on a proximal end side of the insertion portion, the connector portion comprising plural connectors to which an external device is connected; and
a cable portion including:
plural first coaxial lines directly connected to the plural piezoelectric element groups configured to transmit the ultrasound to the first area, the first area being proximate to the instrument channel outlet; and
plural second coaxial lines directly connected to the plural piezoelectric element groups configured to transmit the ultrasound to the second area, the second area being further from the instrument channel outlet than the first area;
wherein the plural first coaxial lines being shorter in length than the plural second coaxial lines such that the plural first coaxial lines are configured to produce a higher resolution image than the plural second coaxial lines; and the plural first coaxial lines and the plural second coaxial lines extend from the plural piezoelectric element groups of the ultrasound transducer to the plural connectors of the connector portion.

2. The ultrasound endoscope according to claim 1, wherein each of the plural connectors comprise:
a substrate to be connected to the external device; and
a connecting terminal that connects the substrate to one of the plural first coaxial lines or one of the plural second coaxial lines.

3. The ultrasound endoscope according to claim 2, wherein each of the plural connectors comprise a plurality of substrates.

4. The ultrasound endoscope according to claim 1, wherein all of the plural first coaxial lines connected to the plural piezoelectric element groups configured to transmit the ultrasound to the first area are shorter in length than the plural second coaxial lines connected to the plural piezoelectric element groups configured to transmit the ultrasound to the second area.

5. The ultrasound endoscope according to claim 1, wherein in the cable portion, the shorter a shortest distance from one of the plural piezoelectric element groups to the first area is, the shorter in length a coaxial line connected to the one of the plural piezoelectric element groups is.

6. The ultrasound endoscope according to claim 1, wherein in the cable portion, the closer one of the plural piezoelectric element groups is positioned to a center of the plural piezoelectric element groups that have been arranged, the shorter in length a coaxial line connected to the one of the plural piezoelectric element groups is, the one of the plural piezoelectric element groups being one of the plural piezoelectric element groups configured to transmit the ultrasound to the first area.

7. The ultrasound endoscope according to claim 1, wherein a length of the cable portion corresponding to each of the plural piezoelectric element groups is directly proportional to a distance of each of the plural piezoelectric element groups from the instrument channel outlet.

8. An ultrasound endoscope, comprising:
an insertion portion configured to be inserted into a subject;
an ultrasound transducer provided at a distal end of the insertion portion, the ultrasound transducer comprising plural piezoelectric element groups comprising:
a first piezoelectric element group disposed at a most distal end of the ultrasound transducer; and
a second piezoelectric element group disposed proximally relative to the first piezoelectric element group;
the first piezoelectric element group and the second piezoelectric element group being configured to transmit and receive ultrasound;
a connector portion provided on a proximal end side of the insertion portion, the connector portion comprising plural connectors to which an external device is connected; and
a cable portion including:
first coaxial lines directly connected to the first piezoelectric element group, and
second coaxial lines directly connected to the second piezoelectric element group, the second coaxial lines being shorter in length than the first coaxial lines such that the second coaxial lines are configured to produce a higher resolution image than the first coaxial lines.

9. The ultrasound endoscope according to claim 8, further comprising an instrument channel configured to accommodate an instrument therein, the instrument channel having an instrument channel outlet from which the instrument protrudes, the instrument channel outlet being disposed proximally relative to the ultrasound transducer.

10. The ultrasound endoscope according to claim 9, wherein in the cable portion, the shorter a shortest distance from one piezoelectric element of the second piezoelectric element group to the instrument channel outlet, the shorter in length a coaxial line connected to the one piezoelectric element of the second piezoelectric element group is.

11. The ultrasound endoscope according to claim 9, wherein in the cable portion, the shorter a shortest distance from one piezoelectric element of the first piezoelectric element group to the instrument channel outlet, the shorter in length a coaxial line connected to the one piezoelectric element of the first piezoelectric element group is.

12. The ultrasound endoscope according to claim 11, wherein a length of the cable portion corresponding to each of the plural piezoelectric element groups is directly proportional to a distal location of each of the plural piezoelectric element groups.

13. An ultrasound endoscope, comprising:
an insertion portion configured to be inserted into a subject;
an ultrasound transducer provided at a distal end of the insertion portion, the ultrasound transducer comprising plural piezoelectric element groups configured to transmit ultrasound to a first area and to a second area and to receive the ultrasound from the first area and from the second area;
an instrument channel configured to accommodate an instrument therein, the instrument channel having an instrument channel outlet from which the instrument protrudes, the instrument channel outlet being disposed proximally relative to the ultrasound transducer;
a connector provided on a proximal end side of the insertion portion, the connector comprising plural connectors to which an external device is connected;
a cable including:
plural first coaxial lines directly connected to the plural piezoelectric element groups configured to transmit the ultrasound to the first area, the first area being proximate to the instrument channel outlet; and
plural second coaxial lines directly connected to the plural piezoelectric element groups configured to transmit the ultrasound to the second area, the second area being further from the instrument channel outlet than the first area;
wherein the plural first coaxial lines are configured to produce a higher resolution image than the plural second coaxial lines; and
the plural first coaxial lines and the plural second coaxial lines extend from the plural piezoelectric element groups to the plural connectors.

* * * * *